US008501267B2

(12) United States Patent
Yadav et al.

(10) Patent No.: US 8,501,267 B2
(45) **Date of Patent: *Aug. 6, 2013**

(54) NANOCOMPOSITES

(75) Inventors: Tapesh Yadav, Longmont, CO (US); Clayton Kostelecky, Longmont, CO (US); Evan Franke, Longmont, CO (US); Bijan Miremadi, Longmont, CO (US); Ming Au, N. Augusta, SC (US); Anthony Vigliotti, Fairless Hills, PA (US)

(73) Assignee: PPG Industries Ohio, Inc., Cleveland, OH (US)

( * ) Notice: Subject to any disclaimer, the term of this patent is extended or adjusted under 35 U.S.C. 154(b) by 106 days.

This patent is subject to a terminal disclaimer.

(21) Appl. No.: 13/036,851

(22) Filed: Feb. 28, 2011

(65) Prior Publication Data

US 2011/0152427 A1 Jun. 23, 2011

Related U.S. Application Data

(60) Continuation of application No. 12/081,115, filed on Apr. 10, 2008, now abandoned, which is a continuation of application No. 10/435,222, filed on May 9, 2003, now Pat. No. 8,389,603, which is a division of application No. 09/790,036, filed on Feb. 20, 2001, now Pat. No. 6,933,331, which is a continuation of application No. 09/083,893, filed on May 22, 1998, now Pat. No. 6,228,904.

(60) Provisional application No. 60/079,225, filed on Mar. 24, 1998, provisional application No. 60/069,935, filed on Dec. 17, 1997, provisional application No. 60/049,077, filed on Jun. 9, 1997.

(51) Int. Cl.

| | |
|---|---|
| ***B05D 5/12*** | (2006.01) |
| ***B32B 9/04*** | (2006.01) |
| ***C08K 3/10*** | (2006.01) |
| ***C08K 3/20*** | (2006.01) |
| ***C08K 3/28*** | (2006.01) |
| ***C08K 3/38*** | (2006.01) |
| ***C08K 9/04*** | (2006.01) |

(52) U.S. Cl.
USPC ............ 427/58; 524/404; 524/419; 524/424; 524/428; 524/429; 523/200; 428/411.1; 977/932

(58) Field of Classification Search
USPC ................ 523/400, 200; 524/404, 419, 424, 524/428, 439; 428/411.1; 427/58
See application file for complete search history.

(56) References Cited

U.S. PATENT DOCUMENTS

| | | | | |
|---|---|---|---|---|
| 5,514,292 | A * | 5/1996 | Sato et al. | 252/68 |
| 5,665,212 | A * | 9/1997 | Zhong et al. | 429/105 |
| 5,714,536 | A * | 2/1998 | Ziolo et al. | 524/430 |
| 5,726,247 | A * | 3/1998 | Michalczyk et al. | 525/102 |
| 5,861,445 | A * | 1/1999 | Xu et al. | 523/116 |
| 6,228,904 | B1 * | 5/2001 | Yadav et al. | 523/210 |
| 6,737,463 | B2 * | 5/2004 | Yadav et al. | 524/435 |
| 6,746,791 | B2 * | 6/2004 | Yadav et al. | 429/491 |
| 6,855,749 | B1 * | 2/2005 | Yadav et al. | 523/105 |
| 6,916,872 | B2 * | 7/2005 | Yadav et al. | 524/430 |
| 7,183,337 | B1 * | 2/2007 | Yadav et al. | 523/200 |
| 7,238,734 | B2 * | 7/2007 | Yadav et al. | 523/210 |
| 7,250,454 | B2 * | 7/2007 | Yadav et al. | 523/200 |
| 7,388,042 | B2 * | 6/2008 | Yadav et al. | 523/200 |

* cited by examiner

*Primary Examiner* — Tae H Yoon
(74) *Attorney, Agent, or Firm* — Bill Kuss

(57) ABSTRACT

Methods for preparing nanocomposites with electrical properties modified by powder size below 100 nanometers. Both low-loaded and highly-loaded nanocomposites are included. Nanoscale coated, un-coated, whisker type fillers are taught. Electrical nanocomposite layers may be prepared on substrates.

16 Claims, 4 Drawing Sheets

XRD spectra of the indium tin oxide nanopowder

NANOCOMPOSITES

CROSS-REFERENCE TO RELATED APPLICATIONS

This application is a continuation of U.S. application Ser. No. 12/081,115, filed Apr. 10, 2008, now abandoned which is a continuation of U.S. application Ser. No. 10/435,222, filed May 9, 2003, now U.S. Pat. No. 8,389,603 which is a divisional of U.S. application Ser. No. 09/790,036, filed Feb. 20, 2001, now U.S. Pat. No. 6,933,331, which is a continuation of U.S. application Ser. No. 09/083,893, filed May 22, 1998, now U.S. Pat. No. 6,228,904, which claims priority to U.S. Provisional Application No. 60/079,225, filed Mar. 24, 1998, which also claims priority to U.S. Provisional Application No. 60/069,935, filed Dec. 17, 1997, which also claims priority to U.S. Provisional Application No. 60/049,077, filed Jun. 5, 1997. Each application in this paragraph is incorporated by reference herein.

FIELD OF THE INVENTION

This invention relates to the use of nanoscale powders as a component of novel composites and devices. By incorporating powders having dimensions less than a characteristic domain size into polymeric and other matrices, nanocomposites with unique properties can be produced.

BACKGROUND

A very wide variety of pure phase materials such as polymers are now readily available at low cost. However, low cost pure phase materials are somewhat limited in the achievable ranges of a number of properties, including, for example, electrical conductivity, magnetic permeability, dielectric constant, and thermal conductivity. In order to circumvent these limitations, it has become common to form composites, in which a matrix is blended with a filler material with desirable properties. Examples of these types of composites include the carbon black and ferrite mixed polymers that are used in toners, tires, electrical devices, and magnetic tapes.

The number of suitable filler materials for composites is large, but still limited. In particular, difficulties in fabrication of such composites often arise due to issues of interface stability between the filler and the matrix, and because of the difficulty of orienting and homogenizing filler material in the matrix. Some desirable properties of the matrix (e.g., rheology) may also be lost when certain fillers are added, particularly at the high loads required by many applications. The availability of new filler materials, particularly materials with novel properties, would significantly expand the scope of manufacturable composites of this type.

SUMMARY

Briefly stated, the present invention is directed to nanocomposites and products wherein the presence of novel nanofillers enhance a wide range of properties. In another aspect, the present invention is directed to methods for preparing nanocomposites that enable nanotechnology applications offering advantages such as superior processability (rheology), thermal conductivity, thermal robustness, electrical conductivity, optical clarity and superior functional performance. In an example method, nanofillers and a substance having a polymer are mixed. Both low-loaded and highly-loaded nanocomposites are contemplated. Nanoscale coated and un-coated fillers may be used. Nanocomposite films may be coated on substrates.

In one aspect, the invention comprises a nanostructured filler, intimately mixed with a matrix to form a nanostructured composite. At least one of the nanostructured filler and the nanostructured composite has a desired material property which differs by at least 20% from the same material property for a micron-scale filler or a micron-scale composite, respectively. The desired material property is selected from the group consisting of refractive index, transparency to light, reflection characteristics, resistivity, permittivity, permeability, coercivity, B-H product, magnetic hysteresis, breakdown voltage, skin depth, curie temperature, dissipation factor, work function, band gap, electromagnetic shielding effectiveness, radiation hardness, chemical reactivity, thermal conductivity, temperature coefficient of an electrical property, voltage coefficient of an electrical property, thermal shock resistance, biocompatibility and wear rate.

The nanostructured filler may comprise one or more elements selected from the s, p, d, and f groups of the periodic table, or it may comprise a compound of one or more such elements with one or more suitable anions, such as aluminum, antimony, boron, bromine, carbon, chlorine, fluorine, germanium, hydrogen, indium, iodine, nickel, nitrogen, oxygen, phosphorus, selenium, silicon, sulfur, or tellurium. The matrix may be a polymer (e.g., poly(methyl methacrylate), poly(vinyl alcohol), polycarbonate, polyalkene, or polyaryl), a ceramic (e.g., zinc oxide, indium-tin oxide, hafnium carbide, or ferrite), or a metal (e.g., copper, tin, zinc, or iron). Loadings of the nanofiller may be as high as 95%, although loadings of 80% or less are preferred. The invention also comprises devices which incorporate the nanofiller (e.g., electrical, magnetic, optical, biomedical, and electrochemical devices).

Another aspect of the invention comprises a method of producing a composite, comprising blending a nanoscale filler with a matrix to form a nanostructured composite. Either the nanostructured filler or the composite itself differs substantially in a desired material property from a micron-scale filler or composite, respectively. The desired material property is selected from the group consisting of refractive index, transparency to light, reflection characteristics, resistivity, permittivity, permeability, coercivity, B-H product, magnetic hysteresis, breakdown voltage, skin depth, curie temperature, dissipation factor, work function, band gap, electromagnetic shielding effectiveness, radiation hardness, chemical reactivity, thermal conductivity, temperature coefficient of an electrical property, voltage coefficient of an electrical property, thermal shock resistance, biocompatibility, and wear rate. The loading of the filler does not exceed 95 volume percent, and loadings of 80 volume percent or less are preferred.

The composite may be formed by mixing a precursor of the matrix material with the nanofiller, and then processing the precursor to form a desired matrix material. For example, the nanofiller may be mixed with a monomer, which is then polymerized to form a polymer matrix composite. In another embodiment, the nanofiller may be mixed with a matrix powder composition and compacted to form a solid composite. In yet another embodiment, the matrix composition may be dissolved in a solvent and mixed with the nanofiller, and then the solvent may be removed to form a solid composite. In still another embodiment, the matrix may be a liquid or have liquid like properties.

Many nanofiller compositions are encompassed within the scope of the invention, including nanofillers comprising one or more elements selected from the group consisting of actinium, aluminum, arsenic, barium, beryllium, bismuth, cadmium, calcium, cerium, cesium, cobalt, copper, dysprosium, erbium, europium, gadolinium, gallium, gold, hafnium, hydrogen, indium, iridium, iron, lanthanum, lithium, magnesium, manganese, mendelevium, mercury, molybdenum, neodymium, neptunium, nickel, niobium, osmium, palladium, platinum, potassium, praseodymium, promethium, protactinium, rhenium, rubidium, scandium, silver, sodium, strontium, tantalum, terbium, thallium, thorium, tin, titanium, tungsten, vanadium, ytterbium, yttrium, zinc, and zirconium.

"Domain size" as that term is used herein, refers to the minimum dimension of a particular material morphology. In the case of powders, the domain size is the grain size. In the case of whiskers and fibers, the domain size is the diameter. In the case of plates and films, the domain size is the thickness.

As used herein, a "nanostructured powder" is one having a domain size of less than 100 nm, or alternatively, having a domain size sufficiently small that a selected material property is substantially different from that of a micron-scale powder, due to size confinement effects (e.g., the property may differ by 20% or more from the analogous property of the micron-scale material). Nanostructured powders often advantageously have sizes as small as 50 nm, 30 nm, or even smaller. Nanostructured powders may also be referred to as "nanopowders" or "nanofillers." A nanostructured composite is a composite comprising a nanostructured phase dispersed in a matrix.

As it is used herein, the term "agglomerated" describes a powder in which at least some individual particles of the powder adhere to neighboring particles, primarily by electrostatic forces, and "aggregated" describes a powder in which at least some individual particles are chemically bonded to neighboring particles.

BRIEF DESCRIPTION OF THE DRAWINGS

The invention is described with reference to the several figures of the drawings, in which.

DETAILED DESCRIPTION

Figure 1:
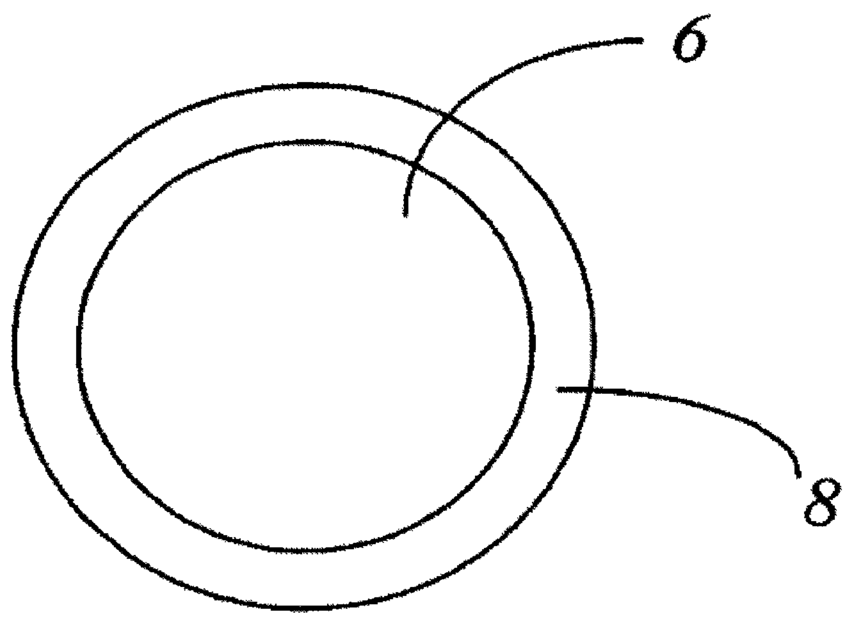
FIG. 1 is a diagram of a nanostructured filler coated with a polymer.

Prior art filler materials for polymeric composites are usually powders with an average dimension in the range of 10-100 μm. Thus, each filler particle typically has on the order of $10^{15}$-$10^{18}$ atoms. In contrast the typical polymer chain has on the order of $10^3$-$10^9$ atoms. While the art of precision manufacturing of polymers at molecular levels is well-developed, the knowledge of precision manufacturing of filler materials at molecular levels has remained largely unexplored.

The number of atoms in the filler particles of the invention (hereinafter called "nanostructured filler" or "nanofiller") is on the order of or significantly less than the number of atoms in the polymer molecules, e.g., $10^2$-$10^{10}$. Thus, the filler particles are comparable in size or smaller than the polymer molecules, and therefore can be dispersed with orders of magnitude higher number density. Further, the fillers may have a dimension less than or equal to the critical domain sizes that determine the characteristic properties of the bulk composition; thus, the fillers may have significantly different physical properties from larger particles of the same composition. This in turn may yield markedly different properties in composites using nanofillers as compared to the typical properties of conventional polymer composites.

These nanostructured filler materials may also have utility in the manufacture of other types of composites, such as ceramic- or metal-matrix composites. Again, the changes in the physical properties of the filler particles due to their increased surface area and constrained domain sizes can yield changes in the achievable properties of composites.

The nanofillers of the invention can be inorganic, organic, or metallic, and may be in the form of powders, whiskers, fibers, plates or films. The fillers represent an additive to the overall composite composition, and may be used at loadings of up to 95% by volume. The fillers may have connectivity in 0, 1, 2, or 3 dimensions. Fillers may be produced by a variety of methods, such as those described in U.S. Pat. Nos. 5,486,675; 5,447,708; 5,407,458; 5,219,804; 5,194,128; and 5,064,464. Particularly preferred methods of making nanostructured fillers are described in U.S. patent application Ser. No. 09/046,465, by Bickmore, et al., filed Mar. 23, 1998, now U.S. Pat. No. 5,984,997 and Ser. No. 08/706,819, by Pirzada, et al., filed Sep. 3, 1996, now U.S. Pat. No. 5,851,507 both of which are incorporated herein by reference.

A wide variety of nanofiller compositions are possible. Some exemplary compositions include metals (e.g., Cu, Ag, Ni, Fe, Al, Pd, and Ti), oxide ceramics (e.g., $TiO_2$, $TiO_{2-x}$, $BaFe_2O_4$, dielectric compositions, ferrites, and manganites), carbide ceramics (e.g., SiC, BC, TiC, WC, $WC_{1-x}$), nitride ceramics (e.g., $Si_3N_4$, TiN, VN, AlN, and $Mo_2N$), hydroxides (e.g., aluminum hydroxide, calcium hydroxide, and barium hydroxide), borides (e.g., $AlB_2$ and $TiB_2$), phosphides (e.g., NiP and VP), sulfides (e.g., molybdenum sulfide, titanium sulfide, and tungsten sulfide), silicides (e.g., $MoSi_2$), chalcogenides (e.g., $Bi_2Te_3$, $Bi_2Se_3$), and combinations of these.

The fillers are immediately mixed with a matrix material, which is preferably polymeric, but may also be ceramic, metallic, or a combination of the above. The matrix may be chosen for properties such as ease of processability, low cost, environmental benignity, commercial availability, and compatibility with the desired filler. The fillers are preferably mixed homogeneously into the matrix, but may also be mixed heterogeneously if desired, for example to obtain a composite having a gradient of some property. Mixing techniques for incorporating powders into fluids and for mixing different powders are well known in the art, and include mechanical, thermal, electrical, magnetic, and chemical momentum transfer techniques, as well as combinations of the above.

The viscosity, surface tension, and density of a liquid matrix material can be varied for mixing purposes, the preferred values being those that favor ease of mixing and that reduce energy needed to mix without introducing any undesirable contamination. One method of mixing is to dissolve the matrix in a solvent which does not adversely affect the properties of the matrix or the filler and which can be easily removed and recovered. Another method is to melt the matrix, incorporate the filler, and cool the mixture to yield a solid composite with the desired properties. Yet another method is to synthesize the matrix in-situ with the filler present. For example, the nanofiller can be mixed with a liquid monomer, which can then be polymerized to form the composite. In this method, the filler may be used as a catalyst or co-catalyst for polymerization. The mixing may also be accomplished in the solid state, for example by mixing a powdered matrix composition with the filler, and then compacting the mixture to form a solid composite.

Mixing can be assisted using various secondary species such as dispersants, binders, modifiers, detergents, and additives. Secondary species may also be added to enhance one to more of the properties of the filler-matrix composite.

Mixing can also be assisted by pre-coating the nanofiller with a thin layer of the matrix composition or with a phase that is compatible with the matrix composition. Such a coated nanoparticle is illustrated in FIG. 1, which shows a spherical nanoparticle 6 and a coating 8. In one embodiment, when embedding nanofillers in a polymer matrix, it may be desirable to coat the filler particles with a related monomer. When mixing nanofillers into a ceramic matrix, pre-coating can be done by forming a ceramic layer around the nanoscale filler particle during or after the synthesis of the nanoscale filler, by methods such as partial oxidation, nitridation, carborization, or boronation. In these methods, the nanostructured filler is exposed to a small concentration of a precursor that reacts with the surface of the filler to form a ceramic coating. For example, a particle may be exposed to oxygen in order to create an oxide coating, to ammonia in order to create a nitride coating, to borane to create a boride coating, or to methane to create a carbide coating. It is important that the amount of precursor be small, to prevent thermal runaway and consequent conversion of the nanostructured filler into a ceramic particle.

In case of polymer matrix, the filler can be coated with a polymer or a monomer by numerous methods, for example, surface coating in-situ, spray drying a dispersion of filler and polymer solution, co-polymerization on the filler surface, and melt spinning followed by milling. A preferred method is surface coating in-situ. In this process, the filler is first suspended in demineralized water (or another solvent) and the suspension's pH is measured. The pH is then adjusted and stabilized with small addition of acid (e.g., acetic acid or dilute nitric acid) or base (e.g., ammonium hydroxide or dilute sodium hydroxide). The pH adjustment produces a charged state on the surface of the filler. Once a desired pH has been achieved, a coating material (for example, a polymer or other appropriate precursor) with opposite charge is introduced into the solvent. This step results in coupling of the coating material around the nanoscale filler and formation of a coating layer around the nanoscale filler. Once the layer has formed, the filler is removed from the solvent by drying, filtration, centrifugation, or any other method appropriate for solid-liquid separation. This technique of coating a filler with another material using surface charge can be used for a variety of organic and inorganic compositions.

When a solvent is used to apply a coating as in the in-situ surface coating method described above, the matrix may also be dissolved in the solvent before or during coating, and the final composite formed by removing the solvent.

A very wide range of material properties can be engineered by the practice of the invention. For example, electrical, magnetic, optical, electrochemical, chemical, thermal, biomedical, and tribological properties can be varied over a wider range than is possible using prior art micron-scale composites.

Nanostructured fillers can be used to lower or raise the effective resistivity, effective permittivity, and effective permeability of a polymer or ceramic matrix. While these effects are present at lower loadings, they are expected to be most pronounced for filler loadings at or above the percolation limit of the filler in the matrix (i.e., at loadings sufficiently high that electrical continuity exists between the filler particles). Other electrical properties which may be engineered include breakdown voltage, skin depth, Curie temperature, temperature coefficient of electrical property, voltage coefficient of electrical property, dissipation factor, work function, band gap, electromagnetic shielding effectiveness and degree of radiation hardness. Nanostructured fillers can also be used to engineer magnetic properties such as the coercivity, B-H product, hysteresis, and shape of the B-H curve of a matrix.

An important characteristic of optical material is its refractive index and its transmission and reflective characteristics. Nanostructured fillers may be used to produce composites with refractive index engineered for a particular application. Gradient lenses may be produced using nanostructured materials. Gradient lenses produced from nanostructured composites may reduce or eliminate the need for polishing lenses. The use of nanostructured fillers may also help filter specific wavelengths. Furthermore, a key advantage of nanostructured fillers in optical applications is expected to be their enhanced transparency because the domain size of nanostructured fillers ranges from about the same as to more than an order of magnitude less than visible wavelengths of light.

The high surface area and small grain size of nanofilled composites make them excellent candidates for chemical and electrochemical applications. When used to form electrodes for electrochemical devices, these materials are expected to significantly improve performance, for example by increasing power density in batteries and reducing minimum operating temperatures for sensors. (An example of the latter effect can be found in copending and commonly assigned U.S. application Ser. No. 08/739,257, "Nanostructured Ion Conducting Solid Electrolytes," by Yadav, et al. now U.S. Pat. No. 5,905,000). Nanostructured fillers are also expected to modify the chemical properties of composites. These fillers are catalytically more active, and provide more interface area for interacting with diffusive species. Such fillers may, for example, modify chemical stability and mobility of diffusing gases. Furthermore, nanostructured fillers may enhance the chemical properties of propellants and fuels.

Many nanostructured fillers have a domain size comparable to the typical mean free path of phonons at moderate temperatures. It is thus anticipated that these fillers may have dramatic effects on the thermal conductivity and thermal shock resistance of matrices into which they are incorporated.

Nanostructured fillers—in coated and uncoated form—and nanofilled composites are also expected to have significant value in biomedical applications for both humans and animals. For example, the small size of nanostructured fillers may make them readily transportable through pores and capillaries. This suggests that the fillers may be of use in developing novel time-release drugs and methods of administration and delivery of drugs, markers, and medical materials. A polymer coating can be utilized either to make water-insoluble fillers into a form that is water soluble, or to make water-soluble fillers into a form that is water insoluble. A polymer coating on the filler may also be utilized as a means to time drug-release from a nanoparticle. A polymer coating may further be used to enable selective filtering, transfer, capture, and removal of species and molecules from blood into the nanoparticle.

A nanoparticulate filler for biomedical operations might be a carrier or support for a drug of interest, participate in the drug's functioning, or might even be the drug itself. Possible administration routes include oral, topical, and injection routes. Nanoparticulates and nanocomposites may also have utility as markers or as carriers for markers. Their unique properties, including high mobility and unusual physical properties, make them particularly well-adapted for such tasks.

In some examples of biomedical functions, magnetic nanoparticles such as ferrites may be utilized to carry drugs to a region of interest, where the particles may then be concentrated using a magnetic field. Photocatalytic nanoparticles can be utilized to carry drugs to region of interest and then photoactivated. Thermally sensitive nanoparticles can similarly be utilized to transport drugs or markers or species of interest and then thermally activated in the region of interest. Radioactive nanoparticulate fillers may have utility for chemotherapy. Nanoparticles suitably doped with genetic and culture material may be utilized in similar way to deliver therapy in target areas. Nanocomposites may be used to assist in concentrating the particle and then providing the therapeutic action. To illustrate, magnetic and photocatalytic nanoparticles may be formed into a composite, administered to a patient, concentrated in area of interest using magnetic field, and finally activated using photons in the concentrated area. As markers, nanoparticulate fillers—coated or uncoated—may be used for diagnosis of medical conditions. For example, fillers may be concentrated in a region of the body where they may be viewed by magnetic resonance imaging or other techniques. In all of these applications, the possibility exists that nanoparticulates can be released into the body in a controlled fashion over a long time period, by implanting a nanocomposite material having a bioabsorbable matrix, which slowly dissolves in the body and releases its embedded filler.

As implants, nanostructured fillers and composites are expected to lower wear rate and thereby enhance patient acceptance of surgical procedures. Nanostructured fillers may also be more desirable than micron-scale fillers, because the possibility exists that their domain size may be reduced to low enough levels that they can easily be removed by normal kidney action without the development of stones or other adverse side effects. While nanoparticulates may be removed naturally through kidney and other organs, they may also be filtered or removed externally through membranes or otherwise removed directly from blood or tissue. Carrier nanoparticulates may be reactivated externally through membranes and reused; for example, nutrient carriers may be removed from the bloodstream, reloaded with more nutrients, and returned to carry the nutrients to tissue. The reverse process may also be feasible, wherein carriers accumulate waste products in the body, which are removed externally, returning the carriers to the bloodstream to accumulate more waste products.

EXAMPLES

Example 1

Indium Tin Oxide Fillers in PMMA

A stoichiometric (90% wt % $In_2O_3$ in $SnO_2$) indium tin oxide (ITO) nanopowder was produced using the methods of copending patent application Ser. No. 09/046,465. 50 g of indium shot was placed in 300 ml of glacial acetic acid and 10 ml of nitric acid. The combination, in a 1000 ml Erlenmeyer flask, was heated to reflux while stirring for 24 hours. At this point, 50 nil of $HNO_3$ was added, and the mixture was heated and stirred overnight. The solution so produced was clear, with all of the indium metal dissolved into the solution, and had a total final volume of 318 ml. An equal volume (318 mL) of 1-octanol was added to the solution along with 600 mL ethyl alcohol in a 1000 mL HDPE bottle, and the resulting mixture was vigorously shaken. 11.25 ml of tetrabutyltin was then stirred into the solution to produce a clear indium/tin emulsion. When the resulting emulsion was burned in air, it produced a brilliant violet flame. A yellow nanopowder residue was collected from the flamed emulsion. The nanopowder surface area was 13.5 $m^2$/gm, and x-ray diffractometer mean grain size was 60 nm.

Figure 2:
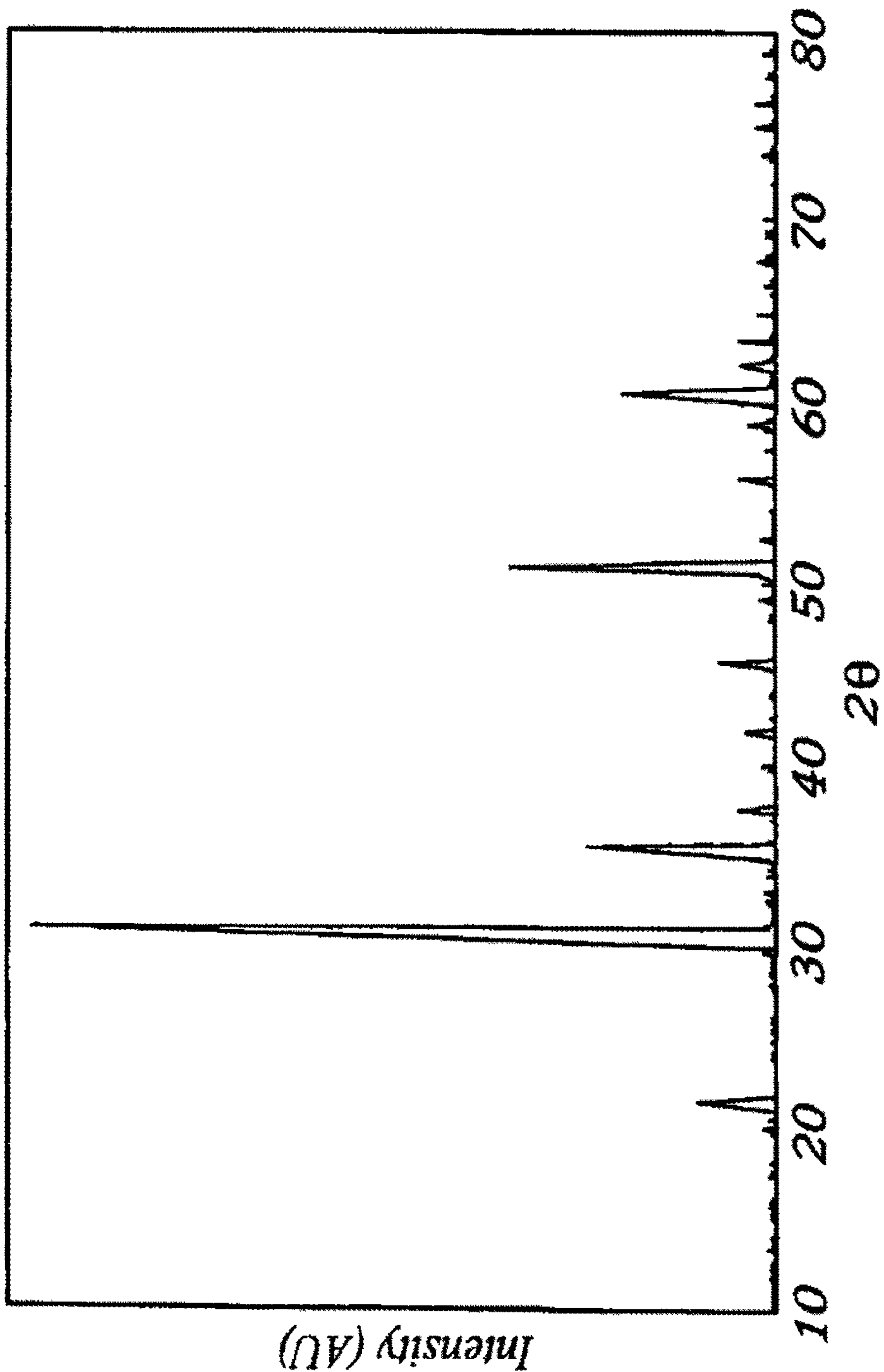
FIG. 2 portrays an X-ray diffraction (XRD) spectrum for the stoichiometric indium tin oxide powder of Example 1.
Figure 3:
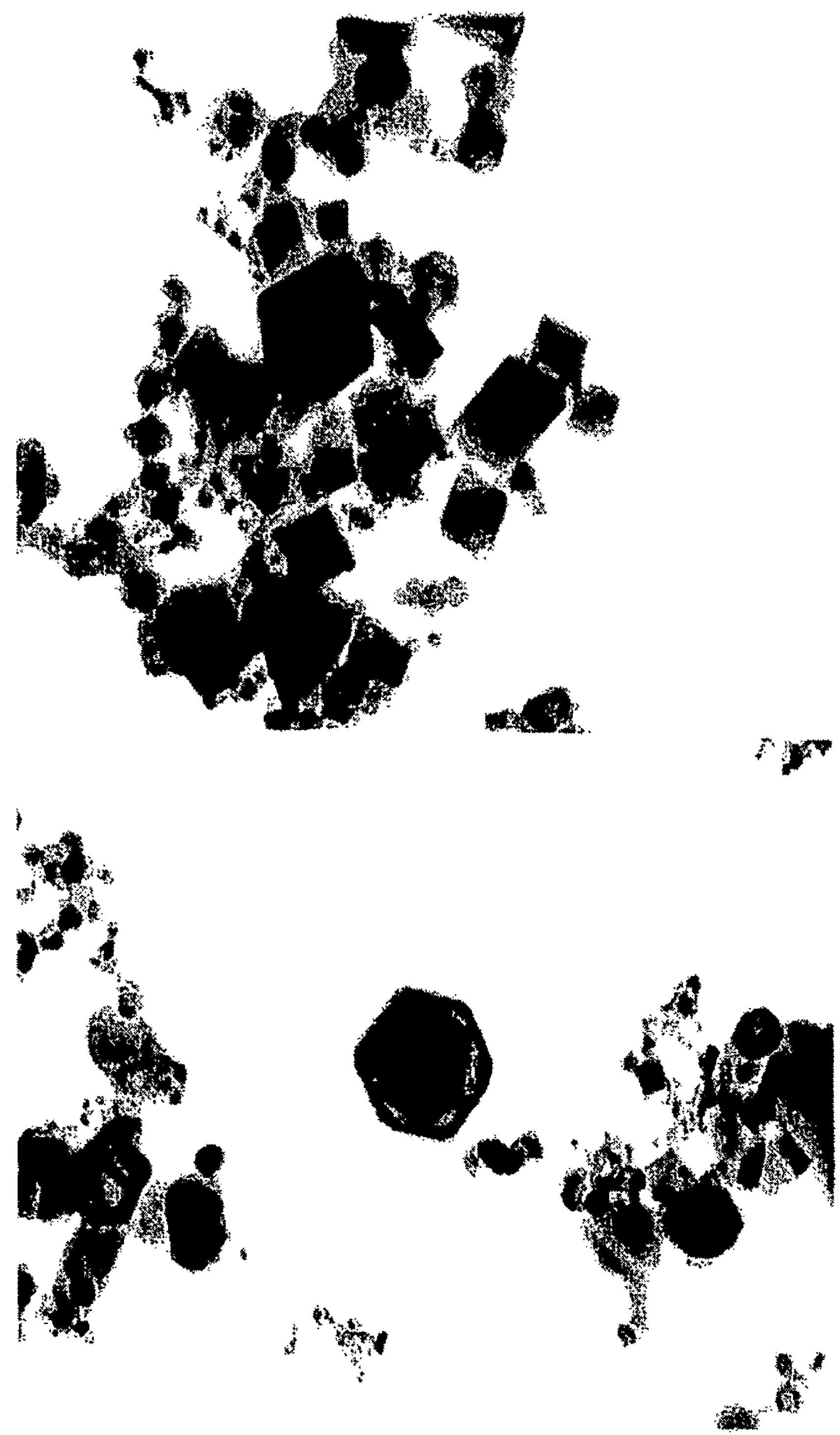
FIG. 3 is a scanning electron microscope (SEM) micrograph of the stoichiometric indium tin oxide powder of Example 1.

FIG. 2 shows the measured X-ray diffraction (XRD) spectrum for the powder, and FIG. 3 shows a scanning electron microscope (SEM image of the powder. These data show that the powder was of nanometer scale.

The nanostructured powder was then mixed with poly(methyl methacrylate) (PMMA) in a ratio of 20 vol % powder to 80 vol % PMMA. The powder and the polymer were mixed using a mortar and pestle, and then separated into three parts, each of which was pressed into a pellet. The pellets were pressed by using a Carver hydraulic press, pressing the mixture into a ¼ inch diameter die using a 1500 pound load for one minute.

After removal from the die, the physical dimensions of the pellets were measured, and the pellets were electroded with silver screen printing paste (Electro Sciences Laboratory 9912-F).

Pellet resistances were measured at 1 volt using a Megohmmeter/IR tester 1865 from QuadTech with a QuadTech component test fixture. The volume resistivity was calculated for each pellet using the standard relation, $$\rho = R\left(\frac{A}{t}\right)$$

where ρ represents volume resistivity in ohm-cm, R represents the measured resistance in ohms, A represents the area of the electroded surface of the pellet in $cm^2$, and t represents the thickness of the pellet in cm. The average volume resistivity of the stoichiometric ITO composite pellets was found to be $1.75\times10^4$ ohm-cm.

Another quantity of ITO nanopowder was produced as described above, and was reduced by passing 2 SCFM of forming gas (5% hydrogen in nitrogen) over the powder while ramping temperature from 25° C. to 250° C. at 5° C./min. The powder was held at 250° C. for 3 hours, and then cooled back to room temperature. The XRD spectrum of the resulting powder indicated that the stoichiometry of the reduced powder was $In_{18}SnO_{29-x}$, with x greater than 0 and less than 29.

The reduced ITO nanopowder was combined with PMMA in a 20:80 volume ratio and formed into pellets as described above. The pellets were electroded as described, and their resistivity was measured. The average resistivity for the reduced ITO composite pellets was found to be $1.09\times10^4$ ohm-cm.

For comparison, micron scale ITO was purchased from Alfa Aesar (catalog number 36348), and was formed into pellets with PMMA and electroded as described above. Again, the volume fraction of ITO was 20%. The average measured resistivity of the micron scale ITO composite pellets was found to be $8.26\times10^8$ ohm-cm, representing a difference of more than four orders of magnitude from the nanoscale composite pellets. It was thus established that composites incorporating nanoscale fillers can have unique properties not achievable by prior art techniques.

Example 2

Hafnium Carbide Fillers in PMMA

Nanoscale hafnium carbide fillers were prepared as described in copending U.S. patent application Ser. Nos.

08/706,819 and 08/707,341. The nanopowder surface area was 53.5 $m^2$/gm, and mean grain size was 16 nm. Micron scale hafnium carbide powder was purchased from Cerac (catalog number H-1004) for comparison.

Composite pellets were produced as described in Example 1, by mixing filler and polymer with a mortar and pestle and pressing in a hydraulic press. Pellets were produced containing either nanoscale or micron scale powder at three loadings: 20 vol % powder, 50 vol % powder, and 80 vol % powder. The pellets were electroded as described above, and their resistivities were measured. (Because of the high resistances at the 20% loading, these pellets' resistivities were measured at 100V. The other pellets were measured at IV, as described in Example 1).

Results of these resistivity measurements are summarized in Table 1. As can be seen, the resistivity of the pellets differed substantially between the nanoscale and micron scale powders. The composites incorporating nanoscale powder had a somewhat decreased resistivity compared to the micron scale powder at 20% loading, but had a dramatically increased resistivity compared to the micron scale powder at 50% and 80% loading.

TABLE 1

| Volume % filler | Resistivity of nanoscale powder composite (ohm-cm) | Resistivity of micron scale powder composite (ohm-cm) |
|---|---|---|
| 20 | $5.54 \times 10^{12}$ | $7.33 \times 10^{13}$ |
| 50 | $7.54 \times 10^{9}$ | $2.13 \times 10^{4}$ |
| 80 | $3.44 \times 10^{9}$ | $1.14 \times 10^{4}$ |

Example 3

Copper Fillers in PMA and PVA

Nanoscale copper powders were produced as described in U.S. patent application Ser. Nos. 08/706,819 and 08/707,341. The nanopowder surface area was 28.1 $m^2$/gm, and mean grain size was 22 nm. Micron scale copper powder was purchased from Aldrich (catalog number 32645-3) for comparison.

The nanoscale and micron scale copper powders were each mixed at a loading of 20 vol % copper to 80 vol % PMMA and formed into pellets as described above. In addition, pellets having a loading of 15 vol % copper in poly(vinyl alcohol) (PVA) were produced by the same method. The pellets were electroded and resistivities measured at 1 volt as described in Example 1. Results are shown in Table 2.

TABLE 2

| Additive | Polymer | Volume % filler | Volume Resistivity (ohm-cm) |
|---|---|---|---|
| nanoscale copper | PMMA | 20 | $5.68 \times 10^{10}$ |
| nanoscale copper | PVA | 15 | $4.59 \times 10^{5}$ |
| micron scale copper | PMMA | 20 | $4.19 \times 10^{12}$ |

It can be seen from Table 2 that the resistivity of the nanoscale copper powder/PMMA composite was substantially reduced compared to the micron scale copper powder/PMMA composite at the same loading, and that the resistivity of the nanoscale copper powder/PVA composite was lower still by five orders of magnitude.

Example 4

Preparation of Polymer-Coated Nanostructured Filler

The stoichiometric (90 wt % $In_2O_3$ in $SnO_2$) indium tin oxide (ITO) nanopowder of Example 1 was coated with a polymer as follows.

200 milligrams of ITO nanopowders with specific surface area of 53 $m^2$/gm were added to 200 ml of demineralized water. The pH of the suspension was adjusted to 8.45 using ammonium hydroxide. In another container, 200 milligrams of poly(methyl methacrylate) (PMMA) was dissolved in 200 ml of ethanol. The PMMA solution was warmed to 100° C. while being stirred. The ITO suspension was added to the PMMA solution and the stirring and temperature of 100° C. was maintained till the solution reduced to a volume of 200 ml. The solution was then cooled to room temperature to a very homogenous solution with very light clear-milky color. The optical clarity confirmed that the powders are still nanostructured. The powder was dried in oven at 120° C. and its weight was measured to be 400 milligrams. The increase in weight, uniformity of morphology and the optical clarity confirmed that the nanopowders were coated with PMMA polymer.

The electrochemical properties of polymer coated nanopowders were different than the as-produced nanopowders. The as-produced nanopowder when suspended in demineralized water yielded a pH of 3.4, while the polymer coated nanopowders had a pH of 7.51.

Example 5

Preparation of Electrical Device Using Nanostructured Fillers

A complex oxide nanoscale filler having the following composition was prepared: $Bi_2O_3$ (48.8 wt %), NiO (24.4 wt %), CoO (12.2 wt %), $Cr_2O_3$ (2.4 wt MnO (12.2 wt %), and $Al_2O_3$ (<0.02 wt %). The complex oxide filler was prepared from the corresponding nitrates of the same cation. The nitrates of each constituent were added to 200 mL of deionized water while constantly stirring. Hydroxides were precipitated with the addition of 50 drops of 28-30% $NH_4OH$. The solution was filtered in a large buchner funnel and washed with deionized water and then with ethyl alcohol. The powder was dried in an oven at 80° C. for 30 minutes. The dried powder was ground using a mortar and pestle. A heat treatment schedule consisting of a 15° C./min ramp to 350° C. with a 30 minute dwell was used to calcine the ground powder.

The nanofiller was then incorporated at a loading of 4% into a zinc oxide ceramic matrix. The composite was prepared by mechanically mixing the doped oxide nanofiller powder with zinc oxide powder, incorporating the mixture into a slurry, and screen printing the slurry (further described below). For comparison, devices were made using both a nanoscale matrix powder produced by the methods of copending and commonly assigned U.S. application Ser. No. 08/706,819, and using a micron scale matrix powder purchased from Chemcorp. The fillers and the matrix powders were mixed mechanically using a mortar and pestle.

Using the filler-added micron scale powder, a paste was prepared by mixing 4.0 g of powder with 2.1 g of a commercial screen printing vehicle purchased from Electro Science Laboratories (ESL vehicle 400). The doped nanoscale powder paste was made using 3.5 g powder and 3.0 g ESL vehicle 400. Each paste was mixed using a glass stir rod. Silver-palladium was used as a conducting electrode material. A screen with a rectangular array pattern was used to print each paste on an alumina substrate. First a layer of silver-palladium powder (the lower electrode) was screen printed on the substrate and dried on a hot plate. Then the ceramic filled powder was deposited, also by screen printing. Four print-dry cycles were used to minimize the possibility of pinhole defects in the varistor. Finally, the upper electrode was deposited.

Figure 4:
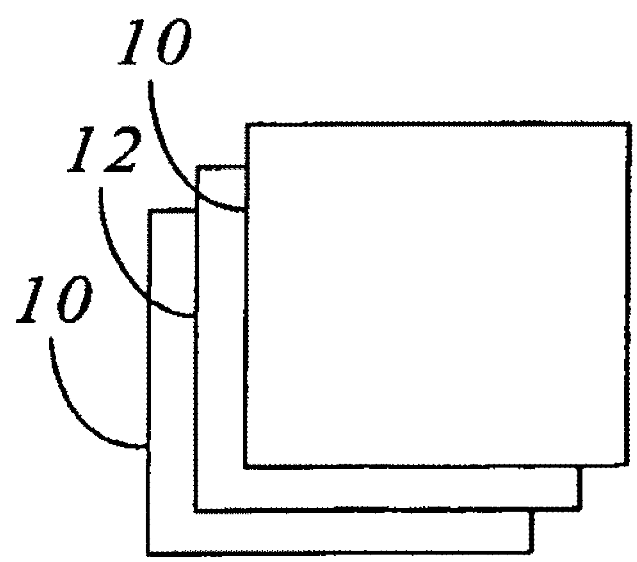
FIG. 4 is a diagram of the nanostructured varistor of Example 5.

The electrode/composite/electrode varistor was formed as three diagonally offset overlapping squares, as illustrated in FIG. 4. The effective nanostructured-filler based composite area in the device due to the offset of the electrodes was 0.036 $in^2$ (0.2315 $cm^2$). The green thick films were co-fired at 900° C. for 60 minutes. The screen printed specimen is shown in FIG. 4, where light squares 10 represent the silver-palladium electrodes, and dark square 12 represents the composite layer.

Silver leads were attached to the electrodes using silver epoxy. The epoxy was cured by heating at a 50° C./min ramp rate to 600° C. and then cooling to room temperature at a rate of 50° C./min. The TestPoint computer software, in conjunction with a Keithley® current source, was used to obtain a current-voltage curve for each of the varistors. Testpoint and Keithley are trademarks or registered trademark of Keithley Scientific Instruments, Inc.

The electrode/micron scale matrix composite/electrode based varistor device had a total thickness of 29-33 microns and a composite layer thickness of 19 microns. The electrode/nanoscale matrix composite/electrode based varistor device had a total thickness of 28-29 microns and a composite layer thickness of 16 microns. Examination of current-voltage response curves for both varistors showed that the nanostructured matrix varistor had an inflection voltage of about 2 volts, while the inflection voltage of the micron scale matrix varistor had an inflection voltage of about 36 volts. Fitting the current-voltage response curves to the standard varistor power-law equation $$I=nV^a \quad (2)$$

yielded values of voltage parameter a of 2.4 for the micron-scale matrix device, and 37.7 for the nanoscale matrix device. Thus, the nonlinearity of the device was shown to increase dramatically when the nanoscale matrix powder was employed.

Example 6

Thermal Battery Electrode Using a Nanostructured Filler

Thermal batteries are primary batteries ideally suited for military ordinance, projectiles, mines, decoys, torpedoes, and space exploration systems, where they are used as highly reliable energy sources with high power density and extremely long shelf life. Thermal batteries have previously been manufactured using techniques that place inherent limits on the minimum thickness obtainable while ensuring adequate mechanical strength. This in turn has slowed miniaturization efforts and has limited achievable power densities, activation characteristics, safety, and other important performance characteristics. Nanocomposites help overcome this problem, as shown in the following example.

Three grams of raw $FeS_2$ powder was mixed and milled with a group of hard steel balls in a high energy ball mill for 30 hours. The grain size of produced powder was 25 nm. BET analysis showed the surface area of the nanopowder to be 6.61 $m^2$/gm. The TEM images confirmed that the ball milled $FeS_2$ powder consists of the fine particles with the round shape, similar thickness and homogenous size. The cathode comprised $FeS_2$ nanopowders (68%), eutectic LiCl—KCl (30%) and $SiO_2$ (2%) (from Aldrich Chemical with 99% purity). The eutectic salts enhanced the diffusion of Li ions and acted as a binder. Adding silicon oxide particles was expected to immobilize the LiCl—KCl salt during melting. For comparison, the cathode pellets were prepared from nanostructured and micron scale $FeS_2$ powders separately.

To improve electrochemical efficiencies and increase the melting point of anode, we chose micron scale Li 44%-Si 56% alloy with 99.5% purity (acquired from Cyprus Foote Mineral) as the anode material in this work. A eutectic salt, LiCl 45%-KCl 55% (from Aldrich Chemical with 99% purity), was selected as electrolyte. The salt was dried at 90° C. and fused at 500° C. To strengthen the pellets and prevent flowing out of electrolyte when it melted, 35% MgO (Aldrich Chemical, 99% purity) powder was added and mixed homogeneously with the eutectic salt powder.

The pellets of anode electrodes were prepared by a cold press process. A hard steel die with a 20 mm internal diameter was used to make the thin disk pellets. 0.314 grams of Li 44%-Si 56% alloy powder (with 76-422 mesh particle size) was pressed under 6000 psi static pressure to form a pellet. The thickness and density of the pellets so obtained was determined to be 0.84 mm and 1.25 g/$cm^2$, respectively. Electrolyte pellets were produced using 0.55 grams of blended electrolyte powder under 4000 psi static pressure. The thickness and density of the pellets obtained were 0.84 mm and 2.08 g/$cm^2$ respectively. The cathode pellet was prepared using 0.91 grams of mixed micron scale $FeS_2$—LiCl—KCl—$SiO_2$ powder pressed under 4000 psi static pressure. The thickness and density of the pellets obtained were 0.86 mm and 3.37 g/$cm^2$, respectively.

A computerized SOLARTRON® 1287 electrochemical interface and a 1260 Gain/Phase Analyzer were employed to provide constant current and to monitor variation in potential between anode and cathode of cells during the discharging. "Solartron" is a registered trademark of the Solartron Electronic Group, Ltd. The cutoff potential of discharge was set at 0.8 volt. The thermal battery with the nanocomposite cathode provided 1 A constant current for 246 seconds, until the potential fell to 0.8 volt. It was observed that the power density of the nanostructured single cell thermal battery was 100% higher than that achievable with micron sized materials. Thus, nanoscale fillers can help enhance the electrochemical performance of such a device.

Example 7

A Magnetic Device Using Nanostructured Ferrite Fillers

Ferrite inductors were prepared using nanostructured and micron-scale powders as follows. One-tenth of a mole (27.3 grams) of iron chloride hexahydrate ($FeCl_3$-$6H_2O$) was dissolved in 500 ml of distilled water along with 0.025 moles (3.24 grams) of nickel chloride ($NiCl_2$) and 0.025 moles (3.41 grams) of zinc chloride ($ZnCl_2$). In another large beaker, 25 grams of NaOH was dissolved in 500 ml of distilled water. While stirring the NaOH solution rapidly, the metal chloride solution was slowly added, forming a precipitate instantaneously. After 1 minute of stirring, the precipitate solution was vacuum filtered while frequently rinsing with distilled water. After the precipitate had dried enough to cake and crack, it was transferred to a glass dish and allowed to dry for 1 hour in an 80° C. drying oven. At this point, the precipitate was ground with a mortar and pestle and calcined in air at 400° C. for 1 hour to remove any remaining moisture and organics.

BET analysis of the produced powder yielded a surface area of 112 $m^2/g$, confirming the presence of nanometer-sized individual particles with an estimated BET particle size of 11 nm. XRD analyses of all nanoscale powders showed the formation of a single (Ni, Zn)$Fe_2O_4$ ferrite phase with peak shapes characteristic of nanoscale powders. XRD peak broadening calculations reported an average crystallite size of 20 nm of the thermally quenched powders and 8 nm for the chemically derived powders. SEM-EDX analyses of sintered nanopowder pellets showed an average composition of 14.8% NiO, 15.8% ZnO, and 69.4% $Fe_2O_3$, which corresponded to the targeted stoichiometric composition of the $Ni_{0.5}Zn_{0.5}Fe_2O_4$.

Nanoscale ferrite filler powders were uniaxially pressed at 5000 pounds in a quarter-inch diameter die set into green pellets. The powders were mixed with 2 weight percent Duramax® binder for improved sinterability. The amount of powder used for pressing varied from 1.5 to 1.7 grams, typically resulting in cylinders having a post-sintered height of approximately 1.5 cm. To avoid cracking and other thermal stress effects, a multi-level heating profile was employed. The pellets were fired at a rate of 5° C./min to 300° C., 10° C./min to 600° C., and 20° C./min to the final sintering temperature, where it was held for four hours. Pellets were cooled from the sintering temperature at a rate of 10° C./min to ensure the sintering temperature ranged from 900° C. to 1300° C., but was typically greater than 1200° C. to ensure an acceptable density. Sintered pellets were then wound with 25 turns of 36 gauge enamel coated wire, the wire ends were stripped, and the completed solenoids where used for electrical characterization. An air coil was prepared for the purpose of calculating magnetic properties. This coil was created by winding 25 turns of the enamel coated wire around the die plunger used previously. This coil was taped with masking tape, slid off the plunger slowly to maintain shape and characteristics, and was characterized along with the ferrite solenoids.

Inductance characterization was performed with a Hewlett-Packard 429A RF Impedance/Materials Analyzer. Impedance, parallel inductance, q factor, and impedance resistance were measured over a logarithmic frequency sweep starting at 1 MHz and ending at 1.8 GHz. Values for permeability (μ) and loss factor (LF) were calculated from inductance (L), air coil inductance ($L_0$), and impedance resistance (R) using the following equations:

$$\mu = \frac{L}{L_0}$$

$$LF = \frac{L_0 R}{\omega L^2}$$

Resistivity measurements were made with a Keithley® 2400 SourceMeter using a four-wire probe attachment and TestPoint™ data acquisition software. Voltage was ramped from 0.1 to 20 volts while simultaneously measuring current. The results were plotted as field (voltage divided by pellet thickness) versus current density (current divided by electrode cross sectional area). The slope of this graph gives material resistivity (ρ).

Table 3 summarizes electrical properties of inductors prepared from micron-sized powder or from nanopowder. In most cases there is an advantage to using nanoscale precursor powder instead of micron-sized powder. It is important to keep in mind that all measurements were taken from cylindrical devices, which have inherently inefficient magnetic properties. Solenoids of this shape were used in this study because of the ease of production and excellent reproducibility. All measured properties would be expected to improve with the use of higher magnetic efficiency shapes such as cores or toroids, or by improving the aspect ratio (length divided by diameter) of the cylindrical samples.

TABLE 3

| | Micron | Nano |
|---|---|---|
| Loss Factor @ 1 MHz | | |
| Average | 0.0032 | 0.0025 |
| Q Factor @ 1 MHz | | |
| Average | 37.2 | 52.2 |
| Critical Frequency | | |
| Average | 68.9 MHz | 78.3 MHz |
| Resistivity | | |
| Average | 0.84 MΩ | 33.1 MΩ |

The inductors made from ferrite nanopowders exhibited significantly higher Q-factor, critical resonance frequency, and resistivity. They also exhibited more than 20% lower loss factor as is desired in commercial applications.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A method for preparing a nanocomposite comprising:

mixing nanofillers with a matrix, wherein the nanofillers have a domain size equal to or less than the mean free path of phonons, and wherein the nanofillers comprise a surface coating of a polymer that is compatible with the matrix;

processing the mixture to produce a solid nanocomposite having a nanoparticle loading of 20% to 80% by volume in a solid polymer matrix; and wherein the nanocomposite has an electrical conductivity that differs by more than 20% as compared with the electrical conductivity exhibited by a composite material of the same composition with filler particles having a domain size of 10 microns.

2. The method of claim 1, wherein the nanofillers have a domain size equal to or less than 100 nanometers.

3. The method of claim 1, wherein the mixing includes adding a secondary species material selected from the group consisting of: dispersants, binders, modifiers, detergents, and additives to enhance one or more properties of the nanocomposite.

4. The method of claim 1, wherein the nanofillers are heterogeneously dispersed in the solid polymer matrix.

5. The method of claim 1, further comprising depositing the nanocomposite on a substrate.

6. The method of claim 1, further comprising applying the nanocomposite as a layer over another substance.

7. The method of claim 1, wherein the nanofillers comprise oxide.

8. The method of claim 1, wherein the nanofillers comprise nitride.

9. The method of claim 1, wherein the nanofillers comprise whiskers.

10. The method of claim 1, wherein the nanofillers comprise one or more elements selected from the group consisting of: aluminum, barium, bismuth, cadmium, calcium, cerium, cesium, cobalt, copper, europium, gallium, gold, indium, iron, lanthanum, lithium, magnesium, manganese, molybdenum, neodymium, nickel, niobium, palladium, platinum, potassium, praseodymium, scandium, silver, sodium, strontium, tantalum, tin, titanium, tungsten, vanadium, ytterbium, yttrium, zinc, and zirconium.

11. The method of claim 1, wherein the nanofillers comprise one or more elements selected from the group consisting of: antimony, boron, bromine, carbon, chlorine, fluorine, germanium, hydrogen, iodine, nitrogen, oxygen, phosphorus, selenium, silicon, sulfur, and tellurium.

12. The method of claim 1, wherein the nanocomposite has an electrical conductivity and a thermal conductivity that differs by more than 20% as compared with the electrical conductivity exhibited by a composite material of the same composition with filler particles having a domain size of 10 microns.

13. The method of claim 1, wherein the matrix comprises monomer, and wherein processing the mixture to produce a solid nanocomposite comprises polymerizing a mixture comprising nanofiller and monomer.

14. The method of claim 1, wherein the matrix comprises a polymer powder, and the mixture comprises the polymer powder and the polymer-coated nanofillers, and wherein processing the mixture to produce a solid nanocomposite comprises compacting the mixture.

15. The method of claim 1, wherein the matrix comprises a polymer material, and the mixture comprises the polymer-coated nanofillers and the polymer material dissolved or dispersed in a solvent, and wherein processing the mixture to produce a solid nanocomposite comprises removing the solvent from the mixture.

16. The method of claim 1, wherein the matrix comprises a liquid polymer, and the mixture comprises the polymer-coated nanofillers and the liquid polymer, wherein processing the mixture to produce a solid nanocomposite comprises solidifying the mixture.

* * * * *